United States Patent
Raguindin et al.

(10) Patent No.: US 10,363,203 B1
(45) Date of Patent: Jul. 30, 2019

(54) METHOD OF USE, AND COMPOSITION OF, FIRST RESPONDER WET WIPES

(71) Applicant: Diamond Wipes International, Inc., Chino, CA (US)

(72) Inventors: Evangeline Raguindin, Chino, CA (US); Jimmy Wang, Chino, CA (US); Denia Dy, Chino, CA (US)

(73) Assignee: DIAMOND WIPES INTERNATIONAL, INC., Chino, CA (US)

( * ) Notice: Subject to any disclaimer, the term of this patent is extended or adjusted under 35 U.S.C. 154(b) by 0 days.

(21) Appl. No.: 15/965,643

(22) Filed: Apr. 27, 2018

Related U.S. Application Data

(60) Provisional application No. 62/490,624, filed on Apr. 27, 2017.

(51) Int. Cl.
| | | |
|---|---|---|
| A61K 8/24 | (2006.01) | |
| A61K 8/02 | (2006.01) | |
| A61K 8/97 | (2017.01) | |
| A61Q 19/10 | (2006.01) | |
| A61K 8/37 | (2006.01) | |
| A61K 8/49 | (2006.01) | |
| A61K 8/34 | (2006.01) | |

(52) U.S. Cl.
CPC .............. *A61K 8/0208* (2013.01); *A61K 8/24* (2013.01); *A61K 8/345* (2013.01); *A61K 8/37* (2013.01); *A61K 8/498* (2013.01); *A61K 8/97* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 2012/0225105 A1* | 9/2012 | Swanzy | A61K 31/70 424/401 |
| 2016/0015031 A1* | 1/2016 | Pesaro | A61K 8/35 424/65 |
| 2016/0100574 A1* | 4/2016 | Pesaro | A01N 31/02 424/48 |

* cited by examiner

*Primary Examiner* — Necholus Ogden, Jr.
(74) *Attorney, Agent, or Firm* — Roy L Anderson

(57) ABSTRACT

A wet wipe useful for removing soot and other potentially dangerous carcinogens from skin surfaces is comprised of a primarily aqueous solution with additional ingredients effective in washing away, rather than embedding, soot and carcinogens in the skin.

6 Claims, No Drawings

METHOD OF USE, AND COMPOSITION OF, FIRST RESPONDER WET WIPES

NOTICE OF RELATED APPLICATIONS

This application is a non-provisional application which claims priority from U.S. Ser. No. 62/490,624, filed Apr. 27, 2018.

FIELD OF THE INVENTION

The present invention is in the field of wipes that can be used in emergency situations and, more particularly, for situations encountered by first responders, especially where soot is present.

BACKGROUND OF THE INVENTION

Fifteen years after 9/11 a number of reports and studies suggest a link between environmental exposures of 9/11 first responders and an increased rate of diseases and cancer for such persons. One concern is soot, which is an environmental exposure that fireman routinely encounter.

Firefighters know soot should be removed as part of a decontamination process after fighting a fire. Because it is not practical to remove clothing and take a shower or fully wash with a chemical wash at the site of a fire, firefighters have used wet wipes to help clean up from firefighting on site. A common wipe used is a simple baby wipe.

A number of companies sell wet wipes for use by firefighters which are advertised as good for use in decontamination by firefighters. Such wipes can contain products designed to moisturize skin and avoid irritation.

SUMMARY OF THE INVENTION

The present invention is generally directed to use of a wet wipe to remove a skin contaminant, such as soot, wherein the wet wipe is soaked with a predominantly aqueous solution in which additional ingredients are added to help remove soot and contaminants from the skin without embedding them within the skin. More particularly, the additional ingredients added to water (which has a wt. % of 90.00 to 98.00), by wt. %, include propanediol (0.10 to 5.00), a blend of extracts for skin-conditioning and soothing (0.001 to 1.00), a natural surfactant blend that softly rinses away dirt/impurities while also providing conditioning for the skin (0.10 to 5.000), a surfactant cleaning agent that also acts as an emulsifier (0.10 to 5.00), a chelating agent that sequesters metallic ions (0.001 to 1.00), a cleaning agent (0.001 to 1.00), a pH adjuster (0.001 to 1.00), an emollient, skin-conditioning, preservative booster (0.001 to 1.00), and preservatives (0.004 to 1.00).

Accordingly, it is primary object of this invention to provide an improved wet wipe useful by firefighters and other persons having skin surfaces contaminated by potentially harmful substances, an example of which is soot.

This and further objects and advantages of the present invention will be apparent to those skilled in the art in connection with the drawing and the detailed description of the invention set forth below.

DETAILED DESCRIPTION OF THE INVENTION

Although wet wipes are sold for use by fire fighters, and some fire fighters use baby wipes for the same purpose, such usage is not always helpful and, indeed, may actually be harmful in some instances. This is because baby wipes and possibly some other wipes as well can actually cause soot and/or carcinogens to embed in skin. Also, while skin care ingredients may be important for cosmetics, a primary objective of first responder wipes should be removal of harmful substances, not skin treatment; this is not to say that skin treatment has no place, just that it must not take primacy over removal of soot and/or carcinogens.

Wet wipes made in accordance with the present invention also have utility outside that of use by firefighters and are also useful by emergency medical technicians and non-professionals, such as consumers, that want a wet wipe effective for use in emergency situations or situations where it may be important to remove a contaminant from skin.

In accordance with the present invention, a preferred embodiment of a wet wipe solution has the following ingredients:

water, by wt. %, within a range of 90.00 to 98.00;
propanediol, by wt. %, within a range of 0.10 to 5.00;
a first blend of extracts, by wt. %, within a range of 0.001 to 1.00;
a natural surfactant blend, by wt. %, within a range of 0.10 to 5.00;
polysorbate 20, by wt. %, within a range of 0.10 to 5.00;
a blend of tetrasodium glutamate diacetate and sodium hydroxide, by wt. %, within a range of 0.001 to 1.00;
trisodium phosphate, by wt. %, within a range of 0.001 to 1.00;
citric acid, by wt. %, within a range of 0.001 to 1.00;
caprylyl glycol, by wt. %, within a range of 0.001 to 1.00;
benzalkonium chloride, by wt. %, within a range of 0.001 to 1.00;
phenoxyethanol, by wt. %, within a range of 0.001 to 1.00;
sodium benzoate, by wt. %, within a range of 0.001 to 1.00; and
potassium sorbate, by wt. %, within a range of 0.001 to 1.00.

An especially preferred blend of extracts includes *chamomilla recutita* (*Matricaria*) flower extract, *cucumis sativus* (cucumber) fruit extract, *althaea officinalis* root extract and *avena sativa* (oat) kernel extract while an especially preferred natural surfactant blend includes decyl glucoside, polyglyceryl-10 caprylate/caprate, coco glucoside, and glyceryl oleata.

In connection with the foregoing embodiment, the various ingredients have the following functions:

1. Decyl Glucoside, Polyglyceryl-10 Caprylate/Caprate, Coco Glucoside, Glyceryl Oleate—a natural surfactant blend that softly rinse away any dirt/impurities and provides conditioning to the skin. Skin is left feeling nourished and smooth.
2. Tetrasodium Glutamate Diacetate—a chelating agent that sequesters metallic ions
3. Propanediol—naturally-derived emollient, humectant, and preservative booster
4. Trisodium Phosphate—cleaning agent
5. Polysorbate 20—a surfactant cleaning agent and also act as an emulsifier
6. Caprylyl Glycol—emollient, skin-conditioning, preservative booster
7. Benzalkonium Chloride, Phenoxyethanol, Sodium Benzoate, Potassium Sorbate—preservatives
8. Citric Acid—pH adjuster
9. Aloe Barbadensis Leaf Extract, *Chamomilla Recutita* (*Matricaria*) Flower Extract, *Cucumis Sativus* (Cucumber) Fruit Extract, *Althaea Officinalis* Root Extract, *Avena Sativa* (Oat) Kernel Extract—an extract blend for skin-conditioning and soothing Also, if desired, fragrance ingredient(s) can be added.

An especially preferred formulation for wet wipes in accordance with the present invention has the following formulation:

| Ingredient | % w/w |
|---|---|
| Water | 91.00-92.00 |
| Propanediol | 5.0000 |
| Aloe Barbadensis Leaf Extract | {This extract blend is added with only |
| Chamomilla Recutita (Matricaria) Flower Extract | {0.000025% of each extract in the blend |
| Cucumis Sativus (Cucumber) Fruit Extract | { |
| Althaea Officinalis Root Extract | { |
| Avena Sativa (Oat) Kernel Extract | { |
| Decyl Glucoside | 0.2000 |
| Polyglyceryl-10 Caprylate/Caprate | 0.0500 |
| Coco Glucoside | 0.0075 |
| Glyceryl Oleate | 0.0075 |
| Polysorbate 20 | 1.0000 |
| Tetrasodium Glutamate Diacetate | 0.0950 |
| Sodium Hydroxide | 0.0010 |
| Trisodium Phosphate | 0.1960 |
| Citric Acid | 0.3450 |
| Caprylyl Glycol | 0.5400 |
| Benzalkonium Chloride | 0.0900 |
| Phenoxyethanol | 0.6600 |
| Sodium Benzoate | {Preservative used in the extract |
| Potassium Sorbate | {blend @ <0.00001% |

While the present invention has been described herein with reference to certain preferred embodiments, these embodiments have been presented by way of example only, and not to limit the scope of the invention. Additional embodiments thereof will be obvious to those skilled in the art having the benefit of this disclosure. Further modifications are also possible in alternative embodiments without departing from the inventive concepts disclosed herein.

Accordingly, it will be readily apparent to those skilled in the art that still further changes and modifications in the actual concepts described herein can readily be made without departing from the spirit and scope of the disclosed inventions.

What is claimed is:

1. A method for decontaminating a skin surface by use of a wet wipe, wherein the wet wipe has a composition consisting essentially of:
   water, by wt. %, within a range of 90.00 to 98.00;
   propanediol, by wt. %, within a range of 0.10 to 5.00;
   a first blend, by wt. %, within a range of 0.001 to 1.00;
   a second blend, by wt. %, within a range of 0.10 to 5.00;
   polysorbate 20, by wt. %, within a range of 0.10 to 5.00;
   a third blend, by wt. %, within a range of 0.001 to 1.00;
   trisodium phosphate, by wt. %, within a range of 0.001 to 1.00;
   citric acid, by wt. %, within a range of 0.001 to 1.00;
   caprylyl glycol, by wt. %, within a range of 0.001 to 1.00;
   benzalkonium chloride, by wt. %, within a range of 0.001 to 1.00;
   phenoxyethanol, by wt. %, within a range of 0.001 to 1.00;
   sodium benzoate, by wt. %, within a range of 0.001 to 1.00; and
   potassium sorbate, by wt. %, within a range of 0.001 to 1.00;
   wherein the first blend consists of the first group consisting essentially of *chamomilla recutita* (*Matricaria*) flower extract, *cucumis sativus* (cucumber) fruit extract, *althaea officinalis* root extract and *avena sativa* (oat) kernel extract;
   wherein the second blend consists of the second group consisting essentially of decyl glucoside, polyglyceryl-10 caprylate/caprate, coco glucoside, and glyceryl oleata; and
   wherein the third blend consists of tetrasodium glutamate diacetate and sodium hydroxide.

2. A method for decontaminating a skin surface by use of a wet wipe, wherein the wet wipe has a composition consisting essentially of:
   water, by wt. %, within a range of 90.00 to 98.00;
   a surfactant blend, by wt. %, within a range of 0.10 to 5.00;
   a chelating agent that sequesters metallic ions, by wt. %, within a range of 0.001 to 1.00;
   an emollient, humectant, and preservative booster, by wt. %, within a range of 0.10 to about 5.00;
   a cleaning agent, by wt. %, within a range of 0.001 to 1.00;
   a surfactant cleaning agent, by wt. %, within a range of 0.10 to 5.00;
   an emollient, by wt. %, within a range of 0.001 to 1.00;
   a preservative, by wt. %, within a range of 0.001 to 4.00;
   a pH adjuster, by wt. %, within a range of 0.001 to 1.00; and
   an extract blend for skin-conditioning and soothing, by wt. %, within a range of 0.001 to 1.00.

3. The method of claim 2 wherein the emollient, humectant and preservative booster consists of propanediol.

4. The method of claim 2 wherein the surfactant cleaning agent also acts as an emulsifier.

5. The method of claim 2 wherein the extract blend consists essentially of *chamomilla recutita* (*Matricaria*) flower extract, *cucumis sativus* (cucumber) fruit extract, *althaea officinalis* root extract and *avena sativa* (oat) kernel extract.

6. The method of claim 2 wherein the surfactant blend consists essentially of decyl glucoside, polyglyceryl-10 caprylate/caprate, coco glucoside, and glyceryl oleate.

* * * * *